(12) United States Patent
Fetzer et al.

(10) Patent No.: US 7,644,618 B2
(45) Date of Patent: Jan. 12, 2010

(54) APPARATUS AND METHOD FOR NONDESTRUCTIVE INSPECTION OF PARTS

(75) Inventors: Barry A. Fetzer, Renton, WA (US); William O. Walters, Seattle, WA (US); Hien T. Bui, Auburn, WA (US)

(73) Assignee: The Boeing Company, Chicago, IL (US)

( * ) Notice: Subject to any disclaimer, the term of this patent is extended or adjusted under 35 U.S.C. 154(b) by 42 days.

(21) Appl. No.: 11/925,193

(22) Filed: Oct. 26, 2007

(65) Prior Publication Data

US 2009/0107244 A1    Apr. 30, 2009

(51) Int. Cl.
*G01N 29/26* (2006.01)

(52) U.S. Cl. .............. 73/632; 73/633; 73/636; 73/640

(58) Field of Classification Search .......... 73/635, 73/620, 622, 625, 627, 628, 629, 633, 634, 73/636, 641
See application file for complete search history.

(56) References Cited

U.S. PATENT DOCUMENTS

| | | | |
|---|---|---|---|
| 4,383,448 A * | 5/1983 | Fujimoto et al. | 73/637 |
| 4,807,476 A | 2/1989 | Cook et al. | |
| 5,203,869 A | 4/1993 | Bashyam | |
| 5,210,485 A * | 5/1993 | Kreiger et al. | 324/758 |
| 5,710,378 A * | 1/1998 | Dykes et al. | 73/601 |
| 6,000,123 A * | 12/1999 | Munezane et al. | 29/740 |
| 6,167,760 B1 | 1/2001 | Brunty et al. | |
| 6,234,024 B1 | 5/2001 | Brunty et al. | |
| 6,260,425 B1 * | 7/2001 | Eder | 73/865.8 |
| 6,484,583 B1 | 11/2002 | Chennell et al. | |
| 6,646,571 B1 * | 11/2003 | Soar et al. | 341/13 |
| 6,658,939 B2 | 12/2003 | Georgeson et al. | |
| 6,848,312 B2 | 2/2005 | Georgeson | |
| 6,993,971 B2 | 2/2006 | Bossi et al. | |
| 7,191,673 B2 * | 3/2007 | Thornhill et al. | 73/865.8 |
| 7,240,556 B2 | 7/2007 | Georgeson et al. | |
| 7,263,889 B2 | 9/2007 | Kennedy et al. | |
| 2007/0217618 A1 * | 9/2007 | Yang et al. | 381/58 |

FOREIGN PATENT DOCUMENTS

| | | | |
|---|---|---|---|
| JP | 363241460 A | * | 6/1988 |
| JP | 405107236 A | * | 4/1993 |

* cited by examiner

*Primary Examiner*—Hezron Williams
*Assistant Examiner*—J M Saint Surin
(74) *Attorney, Agent, or Firm*—Armstrong Teasdale LLP

(57) ABSTRACT

A method of inspecting a radius area of composite parts with an ultrasonic inspection system, the system includes at least one ultrasonic probe, an upper sliding surface, a lower sliding surface, an adjustable guide rail, and an adjustable encoder wheel rotatably coupled to a rotary encoder, is provided. The method includes generating a high frequency sound wave using the probe including a radius of curvature extending from a center point, the sound wave travels partially through the part, adjusting the guide rail to align the center point of the probe with a center axis of a part corner portion, sliding the part through the inspection system to inspect the corner portion using the sound wave by rotating the wheel and rotary encoder such that the arcuate distance of the part is recorded, adjusting the wheel to avoid any apertures defined within the part, and processing the sound wave information.

20 Claims, 8 Drawing Sheets

APPARATUS AND METHOD FOR NONDESTRUCTIVE INSPECTION OF PARTS

BACKGROUND OF THE INVENTION

This disclosure relates generally to test equipment for nondestructive evaluation systems, and more specifically, to ultrasonic inspection devices for the inspection of parts.

As newer materials, such as composite materials, are used in more applications throughout the aircraft industry and other industries, the use of nondestructive test equipment, such as ultrasonic test equipment, to inspect fabricated parts prior to use has become widespread. Ultrasonic test equipment allows an operator to nondestructively inspect the interior of parts, such as fuselage or wing components, for areas of discontinuity such as structural inconsistencies, imperfections, delaminations, and foreign objects introduced during fabrication to name a few.

Ultrasonic test equipment utilizes a high frequency sound wave generated by an ultrasonic transducer, sometimes referred to as a probe, which is located near the surface of the part being tested. The ultrasonic transducer is oriented such that the high frequency sound wave travels through the part, usually in the height or thickness direction. When the sound wave encounters a discontinuity, such as a delamination, or a change in the stiffness of the material, part of the sound energy is reflected. The reflected sound energy travels back through the part and is received by the same ultrasonic transducer, which acts as both a transmitter and receiver in what is commonly referred to as a "pulse echo" ultrasonic test system. Alternatively, the high frequency sound wave generated by the ultrasonic transmitter passes through the entire thickness of the part and is received on the opposite side of the part by a separate receiver in what is commonly known as "through transmission" ultrasonic testing.

The waveform of the received signal from an ultrasonic test is recorded by the test equipment and/or displayed on a monitor or other display device. The data contained in the signal can be displayed in a number of different formats for review by technicians.

In some known ultrasonic inspection devices, a customized part holder is designed for the unique angles and dimensions of each part. The customized part holder is used to hold the part during the inspection process. The fabrication and/or use of multiple part holders may increase the inspection time of the variety of parts. As a result, the efficiency of the inspection process is reduced which may increase the overall cost of inspecting a variety of differently shaped parts.

BRIEF DESCRIPTION OF THE INVENTION

In one aspect, a method of inspecting a radius area of composite parts with an ultrasonic inspection system, where the inspection system includes an inspection device that includes at least one ultrasonic probe, an upper sliding surface, a lower sliding surface, an adjustable guide rail, and an adjustable encoder wheel rotatably coupled to a rotary encoder, is provided. The method includes generating a high frequency sound wave using the at least one ultrasonic probe, the probe including a radius of curvature extending from a center point, wherein the high frequency sound wave travels at least partially through the part, adjusting the guide rail to align the center point of the at least one probe with a center axis of a corner portion of the part, sliding the part through the inspection device to inspect the corner portion of the part using the high frequency sound wave by rotating the encoder wheel and rotary encoder such that the arcuate distance of the part is recorded, adjusting the encoder wheel to avoid any apertures defined within the part, and processing the high frequency sound wave information.

In another aspect, an inspection device for ultrasonic inspection of a variety of differently shaped parts, is provided. The inspection device includes a frame, a support assembly coupled to the frame, the support assembly comprising at least one upper sliding surface and at least one lower sliding surface, an adjustable guide rail rotatably coupled to the frame and positioned adjacent the lower sliding surface such that an angle is defined between the guide rail and the lower sliding surface, and an adjustable encoder assembly slidably coupled to the frame, the adjustable encoder assembly comprising a wheel configured to contact at least one of the inner surface and the outer surface of the part, and a rotary encoder rotatably coupled to the wheel.

In yet another aspect, an ultrasonic inspection system for the inspection of a variety of differently shaped parts, is provided. The ultrasonic inspection system includes a tank at least partially filled with an immersion fluid, an inspection device at least partially submerged within the tank, the inspection device comprising a frame, a support assembly coupled to the frame, the support assembly comprising at least one upper sliding surface and at least one lower sliding surface, an adjustable guide rail rotatably coupled to the frame and positioned adjacent the lower sliding surface such that an angle is defined between the guide rail and the lower sliding surface, and an adjustable encoder assembly slidably coupled to the frame, the adjustable encoder assembly comprising a wheel configured to contact at least one of an inner surface and an outer surface of the part, and a rotary encoder rotatably coupled to the wheel, at least one ultrasonic probe coupled within the inspection device, wherein the at least one ultrasonic probe generates a high frequency sound wave that passes at least partially through a corner portion of the part, and a computer coupled in communication with the rotary encoder and the at least one ultrasonic probe to identify and locate discontinuities within the part.

DETAILED DESCRIPTION OF THE INVENTION

The embodiments herein described generally provide an exemplary apparatus and methods for nondestructive ultrasonic inspection of a variety of parts. The embodiments described herein are not limiting, but rather are examples only. It should be understood that the present invention may apply to the ultrasonic inspection of any type of part or workpiece.

Figure 1:
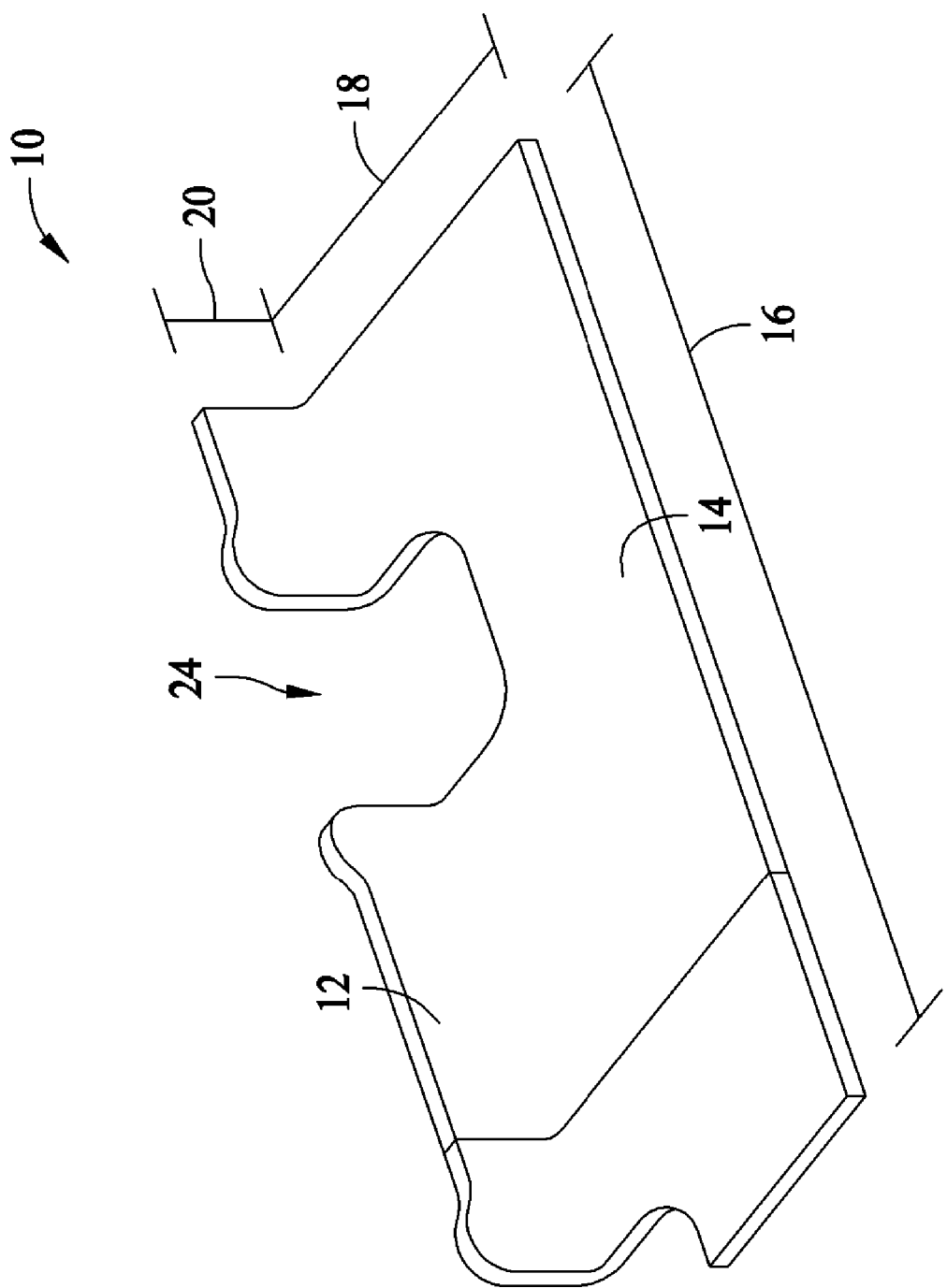
FIG. 1 is a perspective view of an exemplary workpiece.
Figure 2:
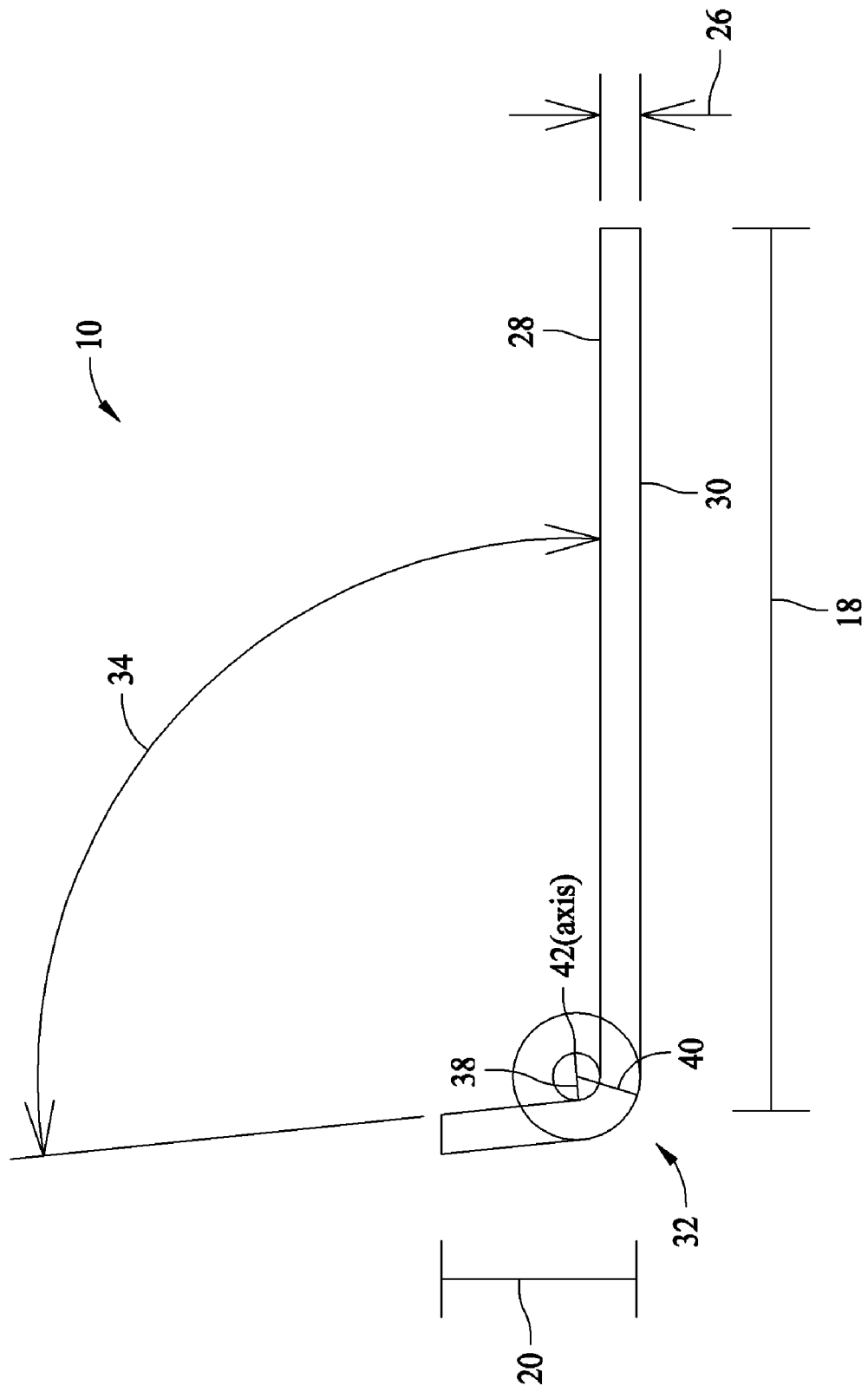
FIG. 2 is a cross-sectional view of the workpiece shown in FIG. 1.

FIG. 1 is a perspective view of an arcuate fuselage workpiece 10. FIG. 2 is a cross-sectional view of workpiece 10. In one embodiment, workpiece 10 may be a fuselage shear-tie. In the illustrated embodiment, workpiece 10 is substantially L-shaped and includes a short side, or flange 12 and a long side, or web 14. Moreover, workpiece 10 has an arcuate length, or distance 16, a web width 18, and a flange height 20. In one embodiment, arcuate distance 16 may extend between about 1 inch to about 96 inches. In another embodiment, web width 18 is between about 1 inch to about 6 inches. Web 14 also has a thickness 26 defined between an inner surface 28 and an outer surface 30 of workpiece 10. Alternatively, thickness 26 may vary along arcuate distance 16 of workpiece 10. In the illustrated embodiment, workpiece 10 includes at least one cutout 24 partially defined within web 14 and partially defined within flange 12. Each cutout 24 facilitates reducing web width 18 of web 14 compared to areas of web 14 that do not include cutouts 24. Alternatively, workpiece 10 may not include any cutouts 24.

Flange 12 extends away from web 14 at a corner portion 32, such that flange 12 is oriented at a web-to-flange angle 34, with respect to web 14. In one embodiment, web-to-flange angle 34 is between about 79° to about 110°. In the illustrated embodiment, web-to-flange angle 34 is about 98°. Moreover, workpiece 10 has an inner corner radius of curvature 38 and an outer corner radius of curvature 40 defined at corner portion 32. Inner corner radius 38 is defined by the substantially arcuate inner surface 28 at corner portion 32 of workpiece 10. Specifically, inner corner radius 38 extends from an axis 42 to inner surface 28 at corner portion 32. Moreover, outer corner radius 40 is defined by the substantially arcuate outer surface 30 at corner portion 32 of workpiece 10. Specifically, outer corner radius 40 extends from axis 42 to outer surface 30 at corner portion 32. In one embodiment, the outer corner radius 40 is about 0.375 inches. In another embodiment, the outer corner radius 40 is about 0.520 inches. The inner corner radius 38 varies, depending on a thickness of corner portion 32. With respect to the above described embodiments, one range of part thicknesses is from about 0.14 inches to about 0.22 inches.

Figure 3:
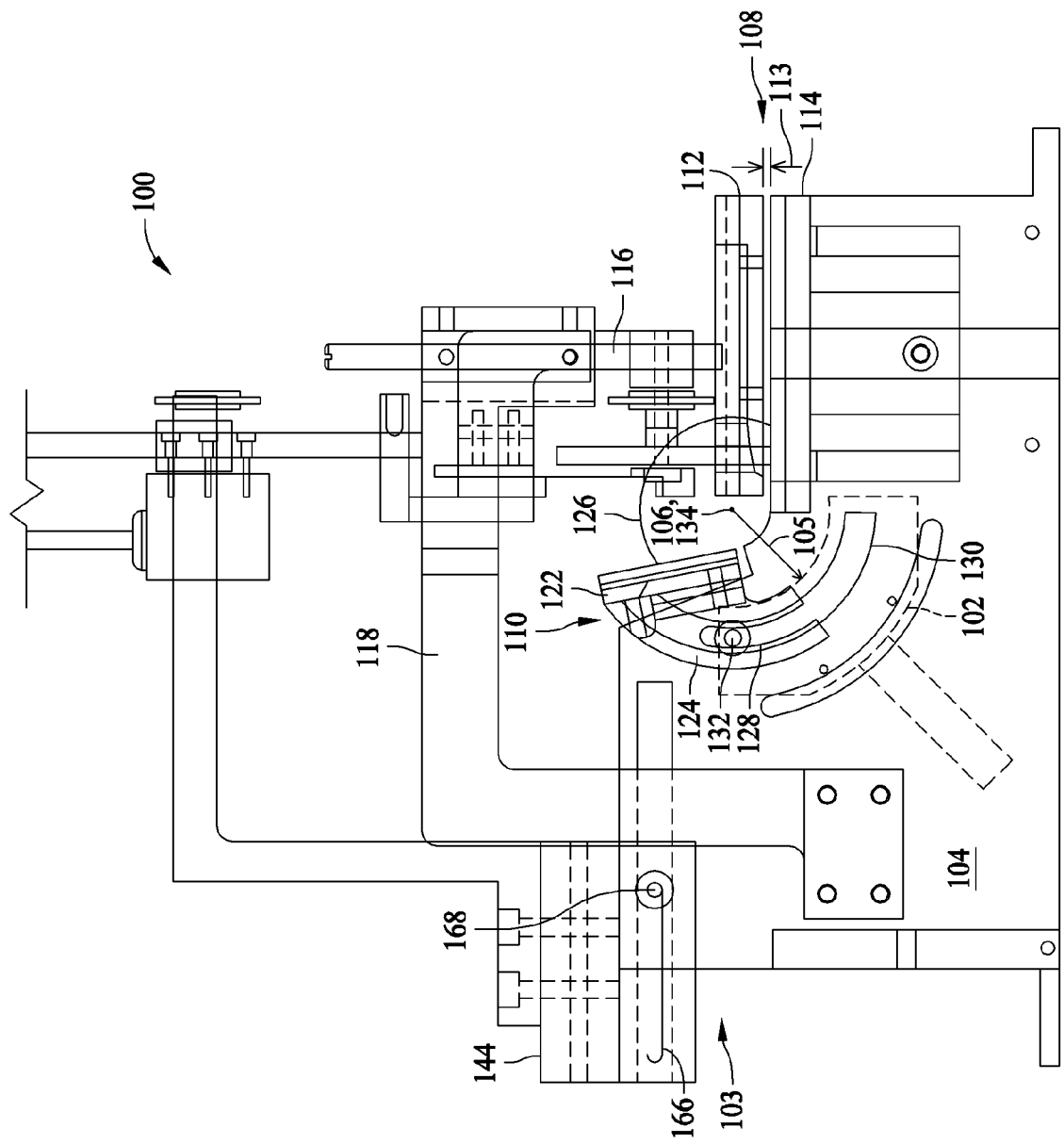
FIG. 3 is a side view of an inspection device for inspecting the workpiece shown in FIG. 1.
Figure 4:
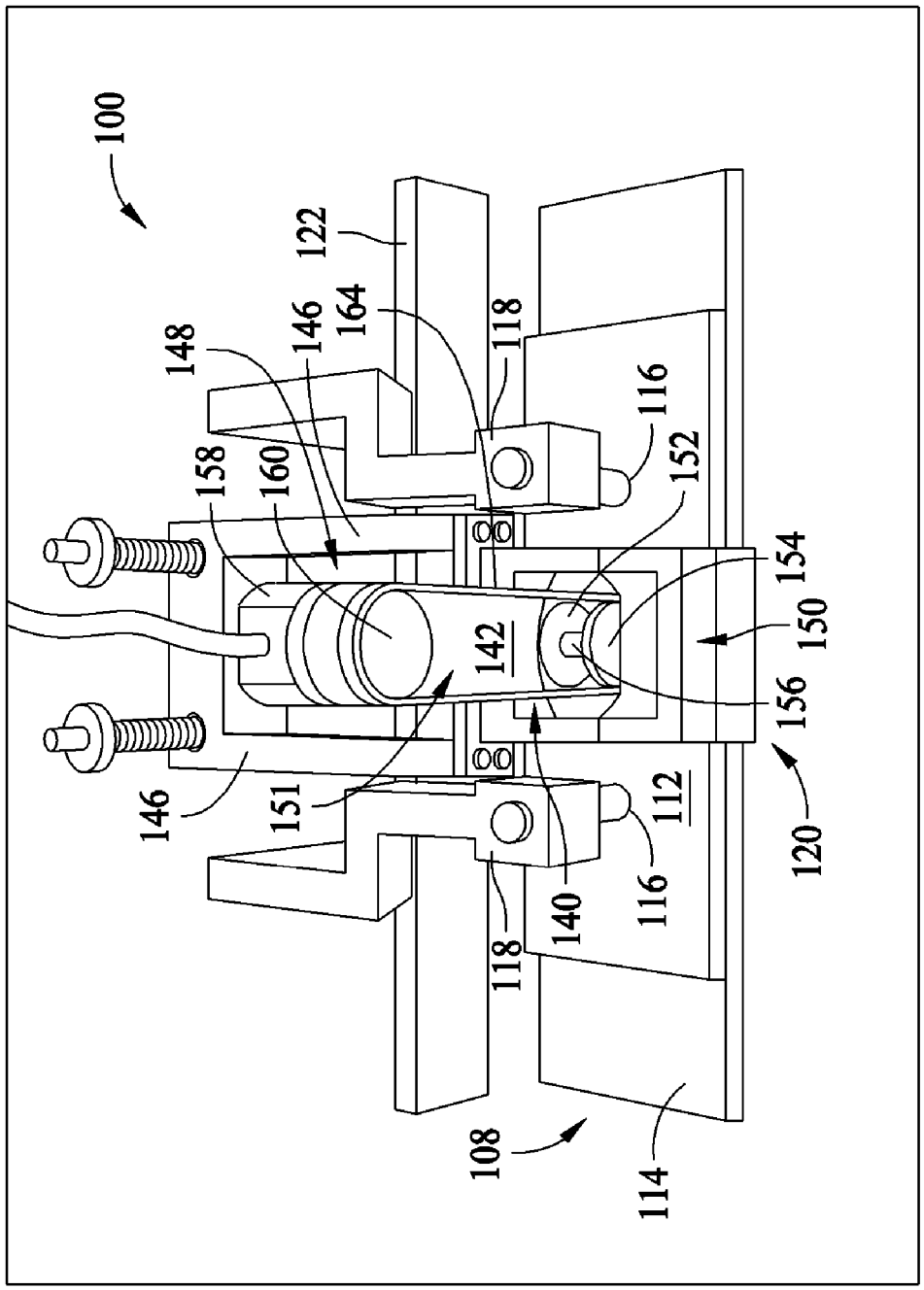
FIG. 4 is a top-front perspective view of the inspection device shown in FIG. 3.
Figure 5:
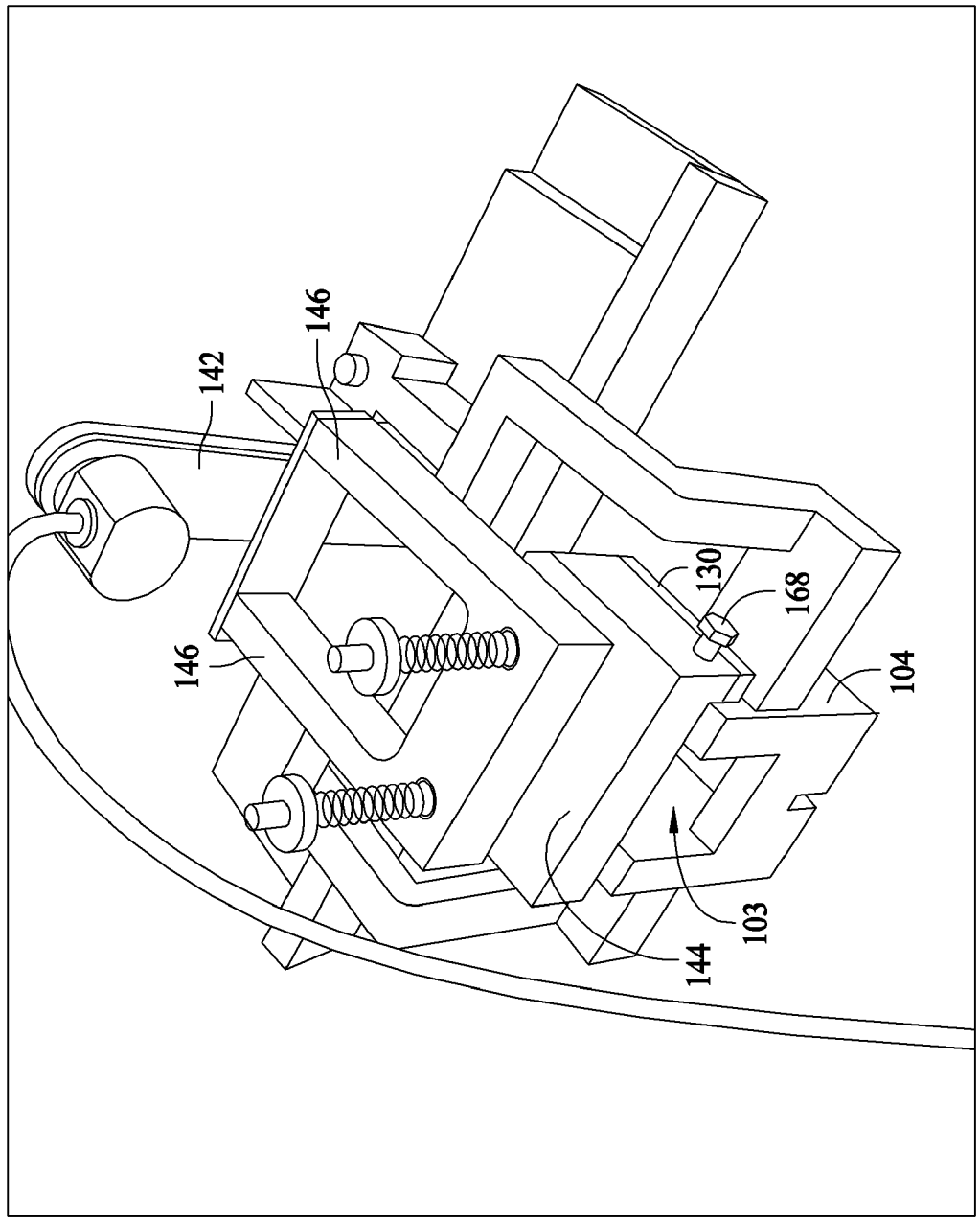
FIG. 5 is a top-rear perspective view of the inspection device shown in FIG. 3.
Figure 6:
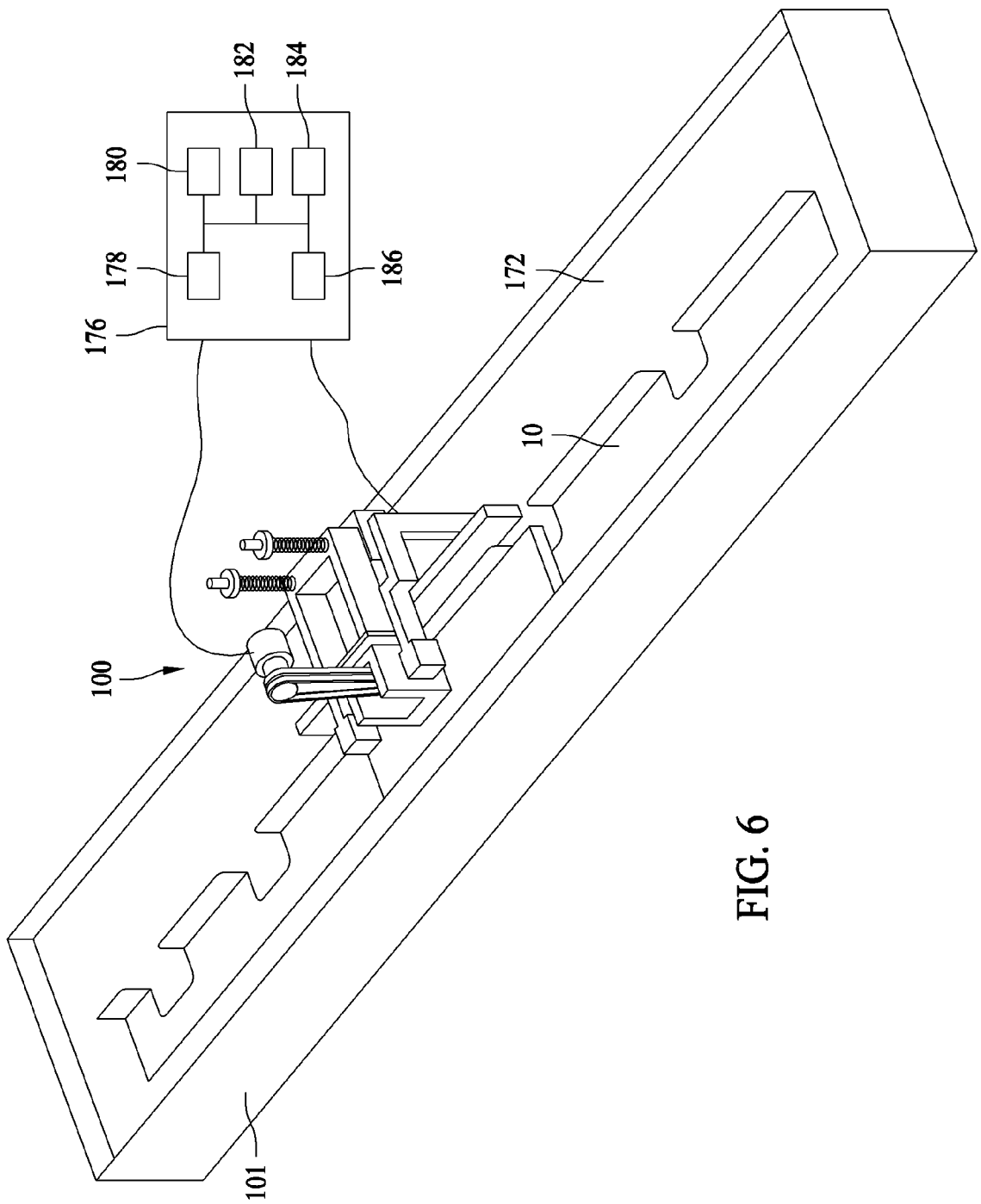
FIG. 6 is a top-front perspective view of the inspection device shown in FIG. 3.

FIG. 3 is a side view of an inspection device 100. FIG. 4 is a top-front perspective view of inspection device 100. FIG. 5 is a top-rear perspective view of inspection device 100. FIG. 6 is a perspective view of inspection device 100 positioned within a tank 101. In the illustrated embodiment, inspection device 100 is a pulse echo ("PE") ultrasonic inspection device that inspects radii 38 and 40 of workpiece 10. Moreover, PE inspection device 100 includes an ultrasonic sensor, or transducer 102 that is coupled within a cavity 103 that is defined within a frame 104. In the illustrated embodiment, transducer 102 is generally arcuate and is operable about an adjustable radius of curvature 105 that extends from a center point 106 towards transducer 102. Transducer 102 is configured to locate areas of discontinuity within workpiece 10, such as but not limited to, voids, areas of high resin porosity, delaminations, foreign matter, or a change in stiffness caused by a composite ply formed of a different material.

In the illustrated embodiment, PE inspection device 100 also includes a pair of stabilizer plates 108 and an adjustable guide rail assembly 110. Stabilizer plates 108 include an upper plate 112 and a lower plate 114. Lower plate 114 is coupled to frame 104 and is positioned adjacent upper plate 112, such that a gap 113 is defined therebetween, wherein gap 113 is configured to receive web 14, as described in more detail below. Upper plate 112 is coupled to a pair of support columns 116 which are coupled to a pair of corresponding support arms 118. Support columns 116 are slidably coupled to arms 118 to facilitate sliding upper plate 112 towards or away from arms 118 in the event thickness 26 of web 14 varies. Specifically, stabilizer plates 108 are configured to slidably couple to web 14 of workpiece 10 to facilitate stabilizing workpiece 10 during inspection, as described in more detail below. In one embodiment, upper plate 112 includes at least one aperture 120 defined therein. Alternatively, an upper plate 112 may include two individual plates, wherein each plate is coupled to a support member such that a gap is defined between each plate.

Adjustable guide rail assembly 110 includes a guide rail 122 coupled to a mounting bracket 124. In one embodiment, guide rail 122 is positioned adjacent stabilizer plates 108 such that an angle 126 is formed between guide rail 122 and lower plate 114. In the illustrated embodiment, guide rail assembly 110 is rotatably coupled to frame 104 using mounting bracket 124. Specifically, mounting bracket 124 includes an arcuate slot 128 defined therein. Moreover, frame 104 includes an arcuate aperture 130 defined therein that is sized and oriented substantially identical to arcuate slot 128. A locking screw 132 extends through arcuate slot 128 and aperture 130 to facilitate locking guide rail assembly 110 in a specific position. Guide rail 122 is adjustable such that guide rail 122 may be oriented at angle 126 that is substantially identical to web-to-flange angle 34 of workpiece 10. Specifically, guide rail 122 may be oriented between about 79° to about 110° with respect to lower plate 114. Moreover, guide rail assembly 110 rotates about an axis of rotation 134 that is substantially coincident with center point 106 of transducer 102.

PE inspection device 100 also includes an adjustable encoder assembly 140 that includes an encoder support member 142 that is coupled to a slide block 144 using a pair of extension arms 146. Support member 142 includes a bottom, or first end 148, an opposite top, or second end 150, and a body 151 extending therebetween. First end 148 includes an encoder wheel 152 coupled thereto, wherein encoder wheel 152 is rotatably coupled to a first gear 154 using a first shaft 156. Moreover, second end 150 includes a rotary encoder 158 coupled thereto, wherein rotary encoder 158 is rotatably coupled to a second gear 160 using a second shaft (not shown). In one embodiment, first gear 154 is rotatably coupled to second gear 160 using a belt 164, such that rotation of first gear 154 facilitates rotation of second gear 160. In an alternative embodiment, first and/or second gear may be a sprocket or any other type of wheel that enables PE inspection device 100 to function as described herein. First end 148 of encoder assembly 140 is positioned adjacent upper plate 112 such that encoder wheel 152 extends at least partially through aperture 120 defined in upper plate 112, as described in more detail below. In the illustrated embodiment, slide block 144 is slidably coupled to frame 104 and includes an elongated aperture 166 defined therein. A locking screw 168 is coupled to frame 104 and extends through elongated aperture 166 to facilitate locking slide block 144, and more specifically, encoder assembly 140 in a specific location.

In one embodiment, PE inspection device 100 may be at least partially submerged within tank 101, and more specifically an immersion fluid 172. PE inspection device 100 is submerged such that an amount of fluid 172 is positioned between workpiece 10 and transducer 102 to facilitate coupling the ultrasonic sound waves to workpiece 10. In an alternative embodiment, the flow of fluid 172 may be channeled between the inspected part and transducer 102 to facilitate coupling the ultrasonic sounds waves to the inspected part. In one embodiment, water is used to couple the ultrasonic sound waves to the inspected part. In another embodiment, any type of fluid may be used that enables PE inspection device 100 to function as described herein. Second end 150 facilitates positioning rotary encoder 158 above the surface of fluid 172 to facilitate preventing fluid 172 from contacting rotary encoder 158.

PE inspection device 100 is electrically coupled to a computer 176 such that information recorded by transducer 102 and/or rotary encoder 158 can be transmitted to computer 176, which facilitates processing the information. Computer 176, in the illustrated embodiment, includes a processor 178, a memory 180, a plurality of inputs 182, and a plurality of outputs 184. As used herein, the term computer is not limited to just those integrated circuits referred to in the art as a computer, but broadly refers to a processor, a microcontroller, a microcomputer, a programmable logic controller, an application specific integrated circuit, and other programmable circuits, and these terms are used interchangeably herein. In one embodiment, memory 180 may include, but is not limited to a random access memory. Alternatively, a computer-readable medium, such as a floppy disk, a compact disc-read only memory (CD-ROM), a magneto-optical disk (MOD), and/or a digital versatile disc (DVD) may also be used. Also, in one embodiment, the plurality of inputs 182 may include, but not limited to, computer peripherals associated with an operator interface such as a mouse (not shown) and/or a keyboard (not shown). Furthermore, in the illustrated embodiment, a plurality of output channels may include, but not be limited to, an operator interface monitor 186.

During operation, workpiece 10 is inserted within PE inspection device 100 such that web 14 is positioned between upper and lower plates 112 and 114, and flange 12 is positioned against guide rail 122. Moreover, angle 126 of guide rail 122 is adjusted using locking screw 132, such that angle 126 is substantially equal to web-to-flange angle 34 of workpiece 10 to facilitate reducing the time required to perform the inspection of multiple workpieces 10 compared to inspection devices that use a unique part holder to inspect each workpiece. As a result, corner portion 32 is positioned adjacent transducer 102 such that axis 42 of workpiece 10 is substantially coincident with center point 106 of transducer 102 and axis of rotation 134 of guide rail 122, to facilitate inspecting corner portion 32, and more specifically, radii 38 and 40.

During inspection of corner portion 32, an operator pushes and/or pulls workpiece 10 through PE inspection device 100. More specifically, web 14 slides between plates 108 such that workpiece 10 is stabilized during inspection. In the event thickness 26 varies, upper plate 112, and more specifically support columns 116, slide towards or away from arms 118. In the illustrated embodiment, PE inspection device 100 is stationary with respect to the inspected part. Alternatively, PE inspection device 100 may be configured to move with respect to a stationary part. In one embodiment, encoder wheel 152 contacts inner surface 28 of web 14, such that movement of workpiece 10 rotates encoder wheel 152, which facilitates rotating first gear 154. The rotation of first gear 154 causes belt 164 to rotate second gear 160, which facilitates rotating rotary encoder 158. Rotary encoder 158 records the arcuate distance 16 of workpiece 10 that passes through PE inspection device 100. Moreover, rotary encoder 158 transmits the recorded information to computer 176, wherein the information is processed.

In the event cutout 24 is positioned within a path of encoder wheel 152, the operator moves encoder assembly substantially away from flange 12, and more specifically cutout 24 such that encoder wheel remains in contact with web 14. Specifically, the operator slides slide block 144, and more specifically encoder wheel 152, away from cutout 24 such that encoder wheel 152 remains in contact with web 14 and continues to record the arcuate distance 16 of workpiece 10 that passes through PE inspection device 100. The operator may secure slide block 144 in a specific position using locking screw 168.

As workpiece 10 is pushed and/or pulled through PE inspection device 100, a high frequency sound wave (not shown) generated by transducer 102 passes through fluid 172 and enters workpiece 10 and more specifically corner portion 32. As the high frequency sound wave passes through workpiece 10 at corner portion 32, the sound wave comes into contact with any areas of discontinuity located in the path of the sound wave. Contact by the sound wave with areas of discontinuity causes at least a portion of the sound wave to be reflected back through workpiece 10 towards transducer 102.

Transducer 102 is configured to transmit and receive ultrasonic sound waves. The received sound waves are recorded and/or transmitted to computer 176. Specifically, the time the sound wave is transmitted and received, and the amplitude of the received sound wave are recorded. Generally, the time between transmission and reception of the sound wave is related to a depth of the discontinuity. Moreover, the amplitude of the received sound wave is generally related to the magnitude of the discontinuity. In one embodiment, computer 176 processes the ultrasonic information to determine whether any discontinuities are present within corner portion 32. Moreover, computer 176 processes the recorded information of arcuate distance 16 transmitted from rotary encoder 158 to determine the location of the discontinuity within corner portion 32. Computer 176 displays the discontinuity information and the location of the discontinuity on monitor 186.

The reduced time afforded by the use of adjustable guide rail assembly 110 and adjustable encoder assembly 140 during the inspection of multiple workpieces 10 that include cutouts 24 and a variety of web-to-flange angles 34 facilitates increasing the efficiency of the inspection process. Moreover, an increase in the inspection process facilitates decreasing the cost of inspecting multiple workpieces 10.

Figure 7:
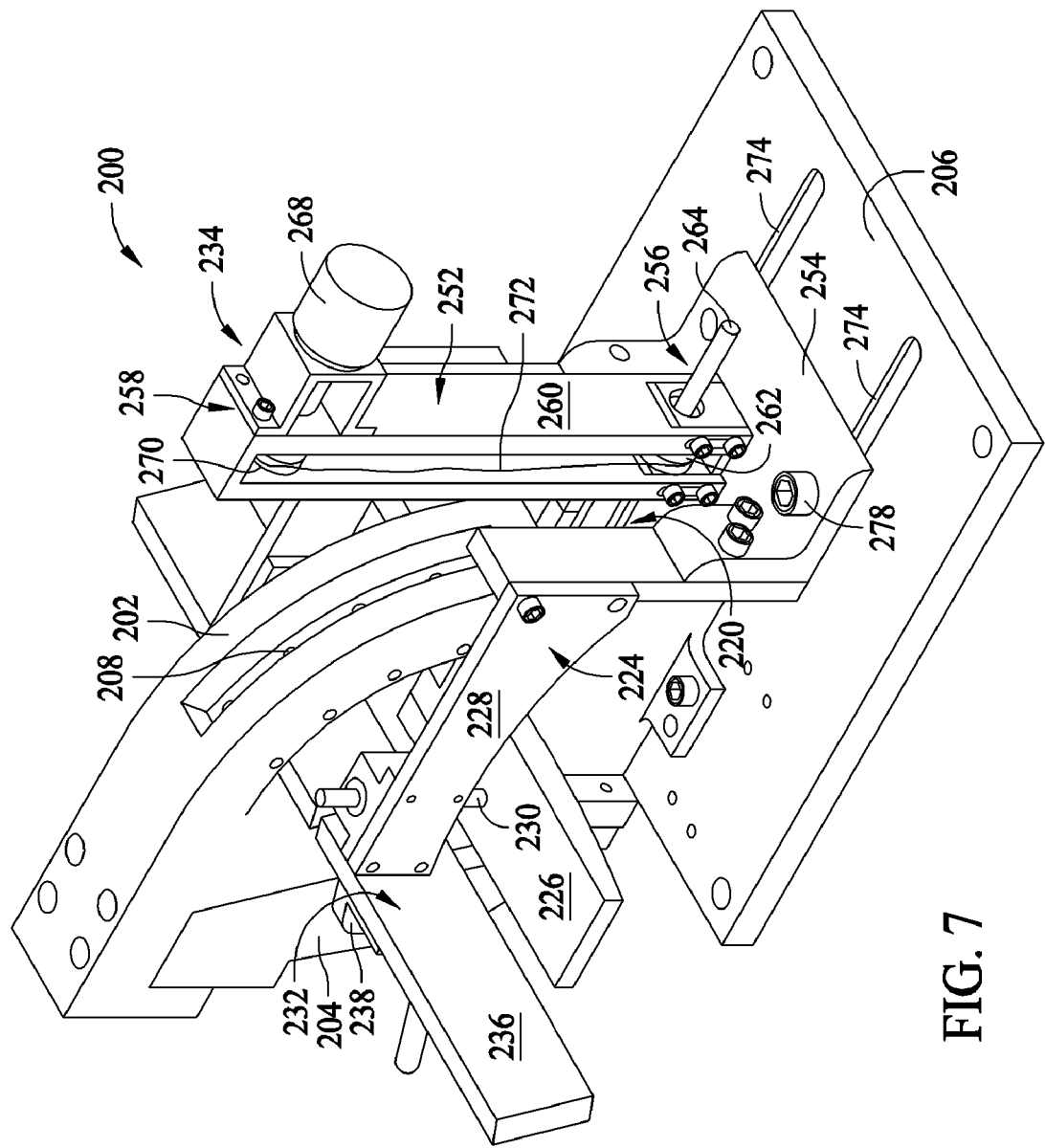
FIG. 7 is a perspective view of another inspection device for inspecting the workpiece shown in FIG. 1.
Figure 8:
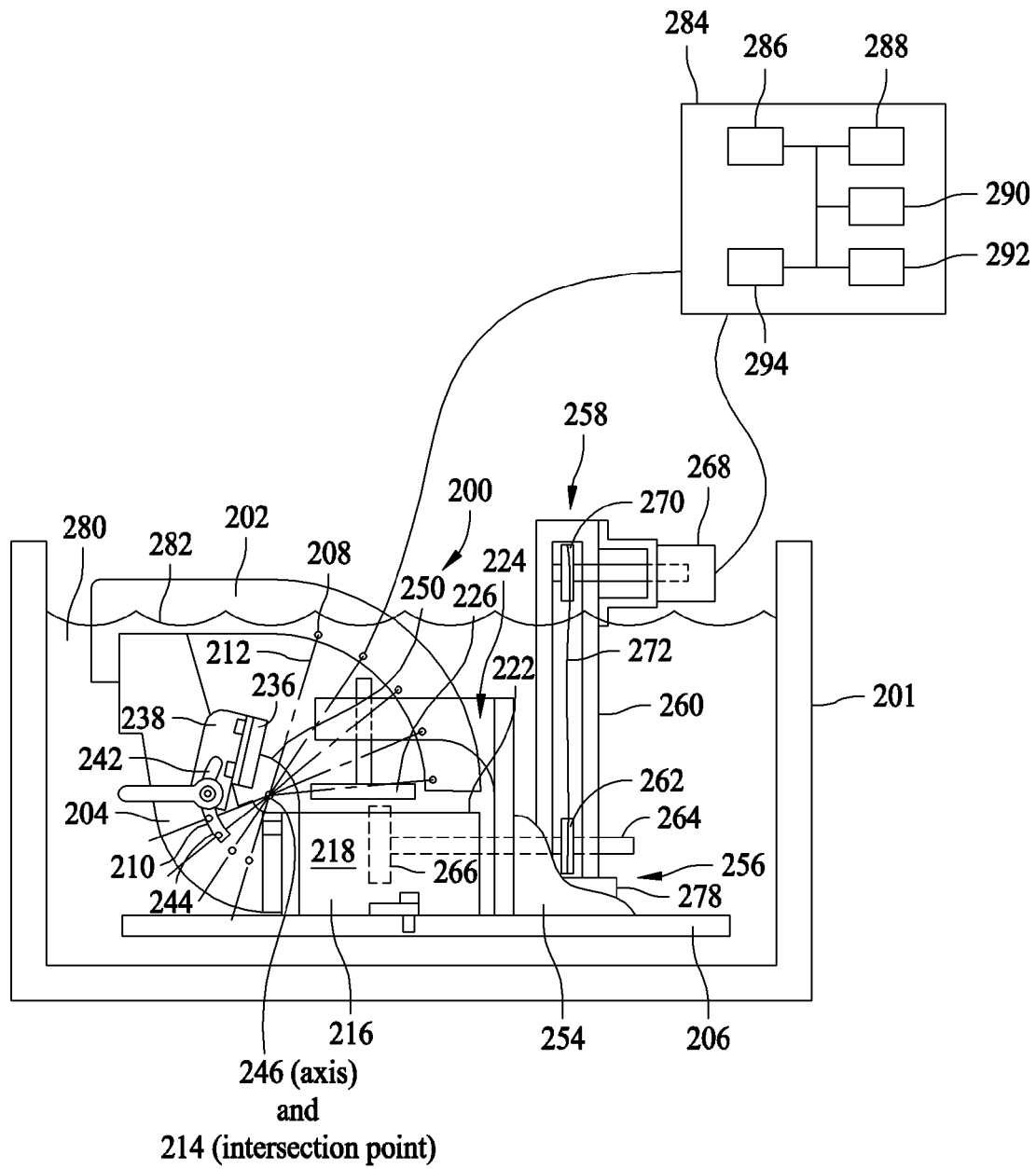
FIG. 8 is a side view of the inspection device shown in FIG. 3.

FIG. 7 is a perspective view of another embodiment of inspection device 200. FIG. 8 is a side view of inspection device 200 partially submerged within a tank 201. In the illustrated embodiment, inspection device 200 is a through transmission ultrasonic ("TTU") device 200 that inspects corner portion 32, and more specifically radii 38 and 40 of workpiece 10. As described herein, the device 200 is operable to inspect parts with varying radii, over a range, without an adjustment of the below described sensors. Moreover, TTU inspection device 200 includes a first arcuate sensor housing 202 coupled to a second arcuate sensor housing 204 that is coupled to a base 206. First arcuate sensor housing 202 is positioned opposite second arcuate sensor housing 204. First arcuate sensor housing 202 includes five first sensors, or transducers 208, and second arcuate sensor housing 204 includes five second transducers 210. In one embodiment, first and second arcuate sensor housings 202 and 204 may include any number of transducers that enable TTU inspection device 200 to function as described herein. In the illustrated embodiment, first arcuate sensor housing 202 is coupled to second arcuate sensor housing 204 such that each first transducer 208 is positioned opposite each corresponding second transducer 210. As a result, each first and each opposite second transducer 208 and 210 form a transducer pair (not shown). More specifically, an ultrasonic beam 212 extends between each transducer pair, wherein each ultrasonic beam 212 intersects at an intersection point 214. Each transducer pair is configured to locate areas of discontinuity within workpiece 10 such as, but not limited to, voids, areas of high resin porosity, delaminations, foreign matter, or a change in stiffness caused by a composite ply formed of a different material.

In one embodiment, TTU inspection device 200 also includes a wheel housing 216 that is coupled to second arcuate sensor housing 204. Wheel housing 216 includes a pair of side members 218 that define a cavity 220 therebetween. Each side member 218 includes a sliding surface 222 that is configured to contact workpiece 10 during inspection. In the illustrated embodiment, TTU inspection device 200 includes a stabilizer plate assembly 224 that includes an upper stabilizer plate 226 coupled to a pair of support arms 228 using a pair of corresponding columns 230. Upper stabilizer plate 226 is positioned above sliding surface 222 such that a gap (not shown) is defined between sliding surface 222 and upper stabilizer plate 226. The gap is configured to receive web 14 of workpiece 10, as described below in more detail. Support columns 230 are slidably coupled to arms 228 such that upper plate 226 may slide towards or away from arms 228 in the event thickness 26 of web 14 varies. Specifically, upper plate 226 and sliding surface 222 of wheel housing 216 are configured to slidably couple to web 14 to facilitate stabilizing workpiece 10 during inspection, as described in more detail below.

TTU inspection device 200 also includes an adjustable guide rail assembly 232 and an adjustable encoder assembly 234. Adjustable guide rail assembly 232 includes a guide rail 236 coupled to a mounting bracket 238. In the illustrated embodiment, guide rail 236 is positioned adjacent sliding surface 222 such that an angle 240 is formed between guide rail 236 and sliding surface 222. Guide rail assembly 232 is rotatably coupled to second arcuate sensor housing 204 using mounting bracket 238. Specifically, mounting bracket 238 includes an arcuate slot 242 defined therein. Moreover, second arcuate sensor housing 204 includes an arcuate aperture 244 that is sized and oriented substantially identical to arcuate slot 242. A locking clamp 248 at least partially extends through arcuate slot 242 and arcuate aperture 244 to facilitate locking guide rail assembly 232 in a specific position. In one embodiment, guide rail 236 is adjustable such that guide rail 236 may be oriented at an angle 250 that is substantially identical to web-to-flange angle 34 of workpiece 10. Specifically, guide rail 236 may be oriented at an angle between about 79° to about 110° with respect to sliding surface 222. Moreover, guide rail assembly 232 rotates about an axis 246 that is substantially coincident with intersection point 214.

In the illustrated embodiment, adjustable encoder assembly 234 includes an encoder support member 252 that is coupled to a slide plate 254. Support member 252 includes a bottom, or first end 256, an opposite top, or second end 258, and a body 260 extending therebetween. A first gear 262 is coupled to a first shaft 264, wherein the first gear 262 and first shaft are coupled to first end 256. First shaft 264 is also coupled to an encoder wheel 266 that is positioned within cavity 220. At least a portion of encoder wheel 266 extends away from wheel housing 216 and more specifically, sliding surface 222 such that encoder wheel 266 contacts workpiece 10 in the event workpiece 10 is inserted within TTU inspection device 200. Moreover, second end 258 includes a rotary encoder 268 coupled thereto, wherein rotary encoder 268 is rotatably coupled to a second gear 270 using a second shaft (not shown). Alternatively, first and/or second gear may be a sprocket or any other type of wheel that enables TTU inspection device 200 to function as described herein. In one embodiment, first gear 262 is rotatably coupled to second gear 270 using a belt 272, such that rotation of first gear 262 facilitates rotation of second gear 270.

Moreover, stabilizer plate assembly 224 and adjustable encoder assembly 234 are couple to slide plate 254, wherein slide plate 254 is slidably coupled to base 206. Specifically, base 206 includes a pair of elongated slots 274 defined therein, and slide plate 254 includes a pair of apertures 276 that are substantially aligned with elongated slots 274. A locking screw 278 extends through each aperture and into each corresponding elongated slot 274 to facilitate locking slide plate 254 in a specific location with respect to base 206.

TTU inspection device 200 may be at least partially submerged within tank 201, and more specifically an immersion fluid 280. TTU inspection device 200 is submerged such that an amount of fluid 280 is positioned between workpiece 10 and first and second transducers 208 and 210 to facilitate coupling ultrasonic sound beams 212 to workpiece 10. Alternatively, the flow of fluid 280 may be channeled between the inspected part and first and second transducers 208 and 210 to facilitate coupling ultrasonic sounds beams 212 to the inspected part. In one embodiment, water is used to couple ultrasonic sound beams 212 to the inspected part. In another embodiment, any type of fluid may be used that enables TTU inspection device 200 to function as described herein. In the illustrated embodiment, second end 258 facilitates positioning rotary encoder 268 above a surface 282 of fluid 280 to facilitate preventing fluid 280 from contacting rotary encoder 268.

TTU inspection device 200 is electrically coupled to computer 284 such that information recorded by transducer 202 and/or rotary encoder 268 can be transmitted to computer 284, which facilitates processing the information. Computer 284, in the illustrated embodiment, includes a processor 286, a memory 288, a plurality of inputs 290, and a plurality of outputs 292. As used herein, the term computer is not limited to just those integrated circuits referred to in the art as a computer, but broadly refers to a processor, a microcontroller, a microcomputer, a programmable logic controller, an application specific integrated circuit, and other programmable circuits, and these terms are used interchangeably herein. In one embodiment, memory 288 may include, but is not limited to a random access memory. Alternatively, a computer-readable medium, such as a floppy disk, a compact disc—read only memory (CD-ROM), a magneto-optical disk (MOD), and/or a digital versatile disc (DVD) may also be used. Also, in one embodiment, the plurality of inputs 290 may include, but not limited to, computer peripherals associated with an operator interface such as a mouse (not shown) and/or a keyboard (not shown). Furthermore, in the illustrated embodiment, a plurality of output channels may include, but not be limited to, an operator interface monitor 294.

During operation, workpiece 10 is inserted within TTU inspection device 200 such that web 14 is positioned between upper plate 226 and sliding surface 222, and flange 12 is positioned against guide rail 236. Moreover, angle 250 of guide rail 236 is adjusted using locking clamp 248, such that angle 250 is substantially equal to web-to-flange angle 34 of workpiece 10 to facilitate reducing the time required to perform the inspection of multiple workpieces 10 compared to inspection devices that use a unique part holder to inspect each workpiece. As a result, corner portion 32 is positioned within TTU inspection device 200 such that axis 246 of workpiece 10 is substantially coincident with intersection point 214 of ultrasonic beams 212, to facilitate inspecting corner portion 32, and more specifically, radii 38 and 40.

During inspection of corner portion 32, an operator pushes and/or pulls workpiece 10 through TTU inspection device 200. More specifically, web 14 slides between upper plate 226 and sliding surface 222 such that workpiece 10 is stabilized during inspection. In the event thickness 26 varies, upper plate 226, and more specifically support columns 230, slide towards or away from arms 228. In the illustrated embodiment, TTU inspection device 200 is stationary with respect to the inspected part. Alternatively, TTU inspection device 200 may be configured to move with respect to a stationary part. In one embodiment, encoder wheel 266 contacts outer surface 30 of web 14, such that movement of workpiece 10 rotates encoder wheel 266, which facilitates rotating first gear 262. The rotation of first gear 262 causes belt 272 to rotate second gear 270 which facilitates rotating rotary encoder 268. Rotary encoder 268 records the arcuate distance 16 of workpiece 10 that passes through TTU inspection device 200. Moreover, rotary encoder 268 transmits the recorded information to computer 284, wherein the information is processed.

In the event cutout 24 is positioned within a path of encoder wheel 266, the operator moves encoder assembly substantially away from flange 12, and more specifically cutout 24 such that encoder wheel remains in contact with web 14. Specifically, the operator slides slide plate 254, and more specifically encoder wheel 266, away from cutout 24 such that encoder wheel 266 remains in contact with web 14 and continues to record the arcuate distance 16 of workpiece 10 that passes through TTU inspection device 200. The operator may secure slide plate 254 in a specific position using locking clamp 248.

As workpiece 10 is pushed and/or pulled through TTU inspection device 200, a high frequency beams 212 are generated by first transducers 208 and pass through fluid 280 and enter workpiece 10 and more specifically corner portion 32. The high frequency beams are received by second transducers 210 that are positioned opposite first transducers 208. Alternatively, second transducers 210 may generate high frequency beams 212 and first transducers may receive high frequency beams 212. As high frequency beams 212 pass through workpiece 10 at corner portion 32, each beam 212 comes into contact with any areas of discontinuity located in the path of the sound wave. Contact by each beam 212 with areas of discontinuity causes at least a change in amplitude and/or frequency of each beam 212 received by second transducers 210.

First and second transducers 208 and 210 are configured to record the received beam 212 information and transmit the information to computer 284. Specifically, the time each beam 212 is transmitted and received, and the amplitude of the received beam 212 are recorded. Generally, the time between transmission and reception of each beam 212 is related to a depth of the discontinuity. Moreover, the amplitude of each received beam 212 is generally related to the magnitude of the discontinuity. In one embodiment, computer 284 processes the ultrasonic information to determine whether any discontinuities are present within corner portion 32. Moreover, computer 284 processes the recorded information of arcuate distance 16 transmitted from rotary encoder 268 to determine the location of the discontinuity within corner portion 32. Computer 284 displays the discontinuity information and the location of the discontinuity on monitor 294.

The reduced time afforded by the use of adjustable guide rail assembly 232 and adjustable encoder assembly 234 during the inspection of multiple workpieces 10 that include cutouts 24 and a variety of web-to-flange angles 34 facilitates increasing the efficiency of the inspection process. Moreover, an increase in the inspection process facilitates decreasing the cost of inspecting multiple workpieces 10.

Exemplary embodiments of ultrasonic inspection devices are described in detail above. The inspection devices are not limited to use with the workpieces described herein, but rather, the inspection devices can be utilized independently and separately from the workpiece components described herein. Moreover, the invention is not limited to the embodiments of the inspection devices described above in detail. Rather, other variations of the inspection devices may be utilized within the spirit and scope of the claims.

While the invention has been described in terms of various specific embodiments, those skilled in the art will recognize that the invention can be practiced with modification within the spirit and scope of the claims.

What is claimed is:

1. A method of inspecting a radius area of composite parts with an ultrasonic inspection system, where the inspection system includes an inspection device that includes at least one ultrasonic probe, an upper sliding surface, a lower sliding surface, an adjustable guide rail, and an adjustable encoder wheel rotatably coupled to a rotary encoder, said method comprising:
   generating a high frequency sound wave using the at least one ultrasonic probe, the probe including a radius of curvature extending from a center point, wherein the high frequency sound wave travels at least partially through the part;
   adjusting the guide rail to align the center point of the at least one probe with a center axis of a corner portion of the part;
   sliding the part through the inspection device to inspect the corner portion of the part using the high frequency sound wave by rotating the encoder wheel and rotary encoder such that the arcuate distance of the part is recorded;
   adjusting the encoder wheel to avoid any apertures defined within the part; and
   processing the high frequency sound wave information.

2. A method in accordance with claim 1 further comprising:
   positioning the part between an upper and a lower sliding surface of the inspection device; and
   channeling a fluid between the at least one ultrasonic probe and the part to couple the ultrasonic sound wave to the part.

3. A method in accordance with claim 2 wherein channeling a fluid between the at least one ultrasonic probe and the part further comprises partially submerging the inspection device within a tank filled with an immersion fluid.

4. A method in accordance with claim 1 further comprising generating and receiving the high frequency sound wave using the at least one ultrasonic probe.

5. A method in accordance with claim 1 further comprising generating the high frequency sound wave using the at least one ultrasonic probe and receiving the high frequency sound waves using at least one other ultrasonic probe.

6. A method in accordance with claim 1 further comprising:
   identifying a location of at least one discontinuity within the part using the high frequency sound wave information and the recorded arcuate distance of the part; and
   outputting the location of the at least one discontinuity within the part.

7. A method in accordance with claim 1 wherein adjusting the guide rail further comprises adjusting the guide rail between about 79° to about 110° with respect to the lower sliding surface.

8. A method in accordance with claim 1 wherein adjusting the encoder wheel further comprises moving the encoder wheel between about 1 inch to about 6 inches away from the flange to maintain the wheel in contact with the part.

9. An inspection device for ultrasonic inspection of a variety of differently shaped parts, said inspection device comprising:
- a frame;
- a support assembly coupled to said frame, said support assembly comprising at least one upper sliding surface and at least one lower sliding surface;
- an adjustable guide rail rotatably coupled to said frame and positioned adjacent said lower sliding surface such that an angle is defined between said guide rail and said lower sliding surface; and
- an adjustable encoder assembly slidably coupled to said frame, said adjustable encoder assembly comprising:
  - a wheel configured to contact at least one of the inner surface and the outer surface of the part; and
  - a rotary encoder rotatably coupled to said wheel.

10. An inspection device in accordance with claim 9 wherein said adjustable guide rail is oriented between about 79° to about 110° with respect to said lower sliding surface.

11. An inspection device in accordance with claim 9 wherein said adjustable guide rail is rotatable about an axis of rotation that is substantially coaxial with a center axis defined by an inner and outer radii of curvature of the part.

12. An inspection device in accordance with claim 9 wherein said adjustable encoder assembly is moveable between about 1 inch to about 6 inches away from a flange of the part.

13. An ultrasonic inspection device in accordance with claim 9 further comprising at least one ultrasonic probe that is configured to generate and receive a high frequency sound wave.

14. An ultrasonic inspection device in accordance with claim 9 further comprising a first ultrasonic probe positioned opposite a second ultrasonic probe, wherein said first ultrasonic probe is configured to generate a high frequency sound wave and said second ultrasonic probe is configured to receive the high frequency sound wave after passing through the part.

15. An ultrasonic inspection system for the inspection of a variety of differently shaped parts, said ultrasonic inspection system comprising:
- a tank at least partially filled with an immersion fluid;
- an inspection device at least partially submerged within said tank, said inspection device comprising:
  - a frame;
  - a support assembly coupled to said frame, said support assembly comprising at least one upper sliding surface and at least one lower sliding surface;
  - an adjustable guide rail rotatably coupled to said frame and positioned adjacent said lower sliding surface such that an angle is defined between said guide rail and said lower sliding surface; and
  - an adjustable encoder assembly slidably coupled to said frame, said adjustable encoder assembly comprising:
    - a wheel configured to contact at least one of an inner surface and an outer surface of the part; and
    - a rotary encoder rotatably coupled to said wheel;
- at least one ultrasonic probe coupled within said inspection device, wherein said at least one ultrasonic probe generates a high frequency sound wave that passes through the immersion fluid and at least partially through a corner portion of the part; and
- a computer coupled in communication with said rotary encoder and said at least one ultrasonic probe, said inspection system operable to identify and locate discontinuities within the part.

16. An ultrasonic inspection system in accordance with claim 15 wherein said adjustable guide rail is oriented between about 79° to about 110° with respect to said lower sliding surface.

17. An ultrasonic inspection system in accordance with claim 15 wherein said adjustable guide rail is rotatable about an axis of rotation that is substantially coaxial with a center axis defined by an inner and outer radii of curvature of the part.

18. An ultrasonic inspection system in accordance with claim 15 wherein said adjustable encoder assembly is moveable between about 1 inch to about 6 inches away from a flange of the part.

19. An ultrasonic inspection system in accordance with claim 15 wherein said at least one ultrasonic probe is configured to generate and receive the high frequency sound wave.

20. An ultrasonic inspection system in accordance with claim 15 further comprising a first ultrasonic probe positioned opposite a second ultrasonic probe, wherein said first ultrasonic probe is configured to generate the high frequency sound wave and said second ultrasonic probe is configured to receive the high frequency sound wave after passing through the part.

* * * * *